United States Patent [19]

Anderson

[11] Patent Number: 4,690,801
[45] Date of Patent: Sep. 1, 1987

[54] DEVICE FOR PERFORMING ENZYME IMMUNOASSAYS

[75] Inventor: Hugh B. Anderson, Toronto, Canada

[73] Assignee: Allelix Inc., Mississauga, Canada

[21] Appl. No.: 870,320

[22] Filed: Jun. 3, 1986

[51] Int. Cl.$^4$ .................... G01N 33/52; G01N 37/00; G01N 21/05

[52] U.S. Cl. .................... 422/68; 356/246; 422/61; 422/100; 422/102; 435/291; 435/301; 436/45; 436/543; 436/807

[58] Field of Search .................... 422/57, 58, 61, 72, 422/102, 100, 68; 436/45, 543, 807; 435/288, 291, 301; 356/246

[56] References Cited

U.S. PATENT DOCUMENTS

| | | | |
|---|---|---|---|
| 3,036,894 | 5/1962 | Forestiere | 422/61 |
| 3,532,470 | 10/1970 | Rochte | 422/61 |
| 3,540,858 | 11/1970 | Rochte et al. | 422/102 |
| 4,065,263 | 12/1977 | Woodbridge III | 422/57 |
| 4,237,234 | 12/1980 | Meuniner | 422/72 |
| 4,390,499 | 6/1983 | Curtis et al. | 422/72 |
| 4,515,889 | 5/1985 | Klose et al. | 422/102 |

*Primary Examiner*—Michael S. Marcus
*Attorney, Agent, or Firm*—Ridout & Maybee

[57] ABSTRACT

An enzyme immunoassay device comprises a disk having a thin flexible membrane applied to one side thereof, the membrane defining a conduit and a plurality of reagent reservoirs. The reservoirs are isolated from one another or from the conduit by frangible seals. An assay tube having an assay reagent bonded to the inner wall thereof is attached to the exit end of the conduit. Means are provided for injecting a test sample into the conduit for flowing thereof through the assay tube. Means are also provided for forcing the contents of each reservoir through the conduit and assay tube in the desired order by causing the rupture of each frangible seal sequentially.

18 Claims, 8 Drawing Figures

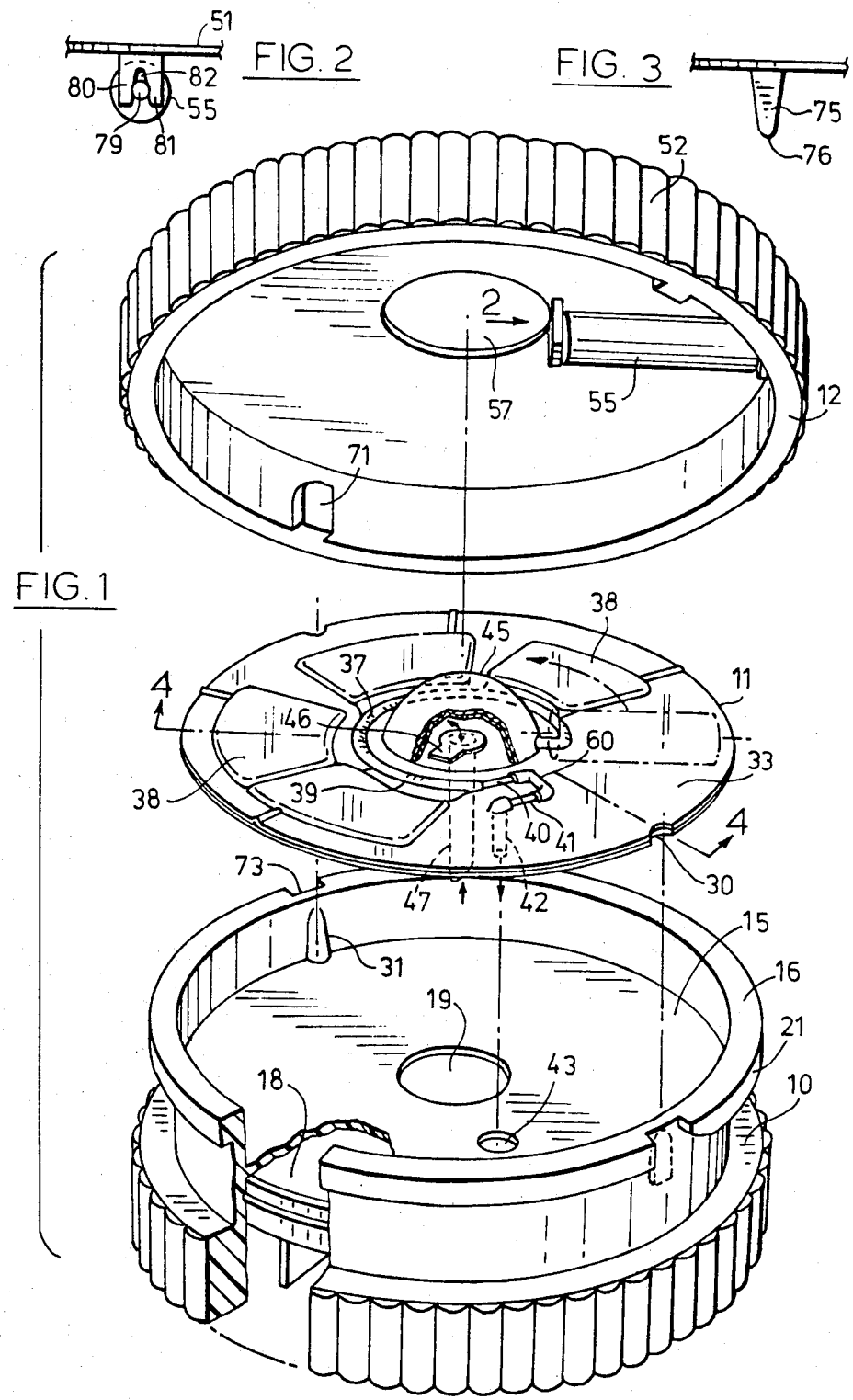

DEVICE FOR PERFORMING ENZYME IMMUNOASSAYS

The present invention relates to a device for performing quantitative or qualitative chemical and immunochemical assays. The device is compact and includes the reagents needed to carry out a specific assay. Operation of the device is designed to be quick and simple and does not rely on the use of electronic or other complicated means. An unskilled person should be able to conduct an assay using the device of the present invention.

The need to obtain quick and accurate assay information is most clearly apparent in medical situations. An enormous number of medical tests or assays are now available, but often the physician or patient must wait hours or even days before such test results can be made available. Samples for testing are often sent to a testing laboratory where skilled technicians employ specially prepared reagents and expensive equipment to obtain the desired data. Assays conducted in this manner are, therefore, expensive as well as slow.

In non-medical applications, test results are often needed quickly for agricultural applications, such as testing for pesticide residues, or for industrial applications, such as testing for the presence of harmful chemicals in the workplace or in products.

The present invention comprises a device for performing assays wherein all of the required reagents are provided in reservoirs which discharge their contents sequentially through a common conduit to a tube in which the assay is carried out. Means are provided for introducing the sample to be tested into the assay tube, and the assay is performed by mechanically causing the contents of each reservoir to pass through the assay tube in the required sequence. The results of the assay may be qualitatively indicated by, for example, the appearance of a color in the assay tube, or may be quantitatively determined by insertion of the assay tube into a suitable analysing instrument.

Because the present device is small and self-contained, only a small sample is required and the test can be conducted by an unskilled person. Likewise, the device will enable the physician, veterinarian or other skilled person to obtain important test results quickly and on the spot.

Accordingly, the present invention provides a device for performing chemical and immunochemical assays, comprising a disk having a thin flexible membrane applied to one side thereof, said membrane defining a conduit and a plurality of reagent reservoirs, each reservoir being isolated from the conduit by at least one frangible seal. An assay tube having one end is attached to an end of the conduit, the assay tube being capable of having an assay reagent bonded to the inner wall thereof. Sample injection means are provided at the other end of the conduit, and means are provided for forcing the contents of each reservoir through the conduit and the assay tube in the desired order by causing the rupture of each frangible seal in the desired sequence. The means for forcing the contents of each reservoir through the conduit also prevent back flow of reagent in the conduit.

BRIEF DESCRIPTION OF THE DRAWINGS

A preferred embodiment of the invention will be described with reference being made to the drawings wherein:

FIG. 1 is an exploded perspective view, partially broken away, of a device in accordance with the invention;

FIG. 2 is a side elevation of a detail taken along arrow 2 in FIG. 1;

FIG. 3 is an alternate embodiment of the same detail shown in FIG. 2;

Referring to FIG. 1, the preferred embodiment of the invention comprises a device having a base 10, a circular disk 11 which fits into the base 10, and a cover 12 which fits over the base 10. The device is generally cylindrical in shape.

Figure 4:
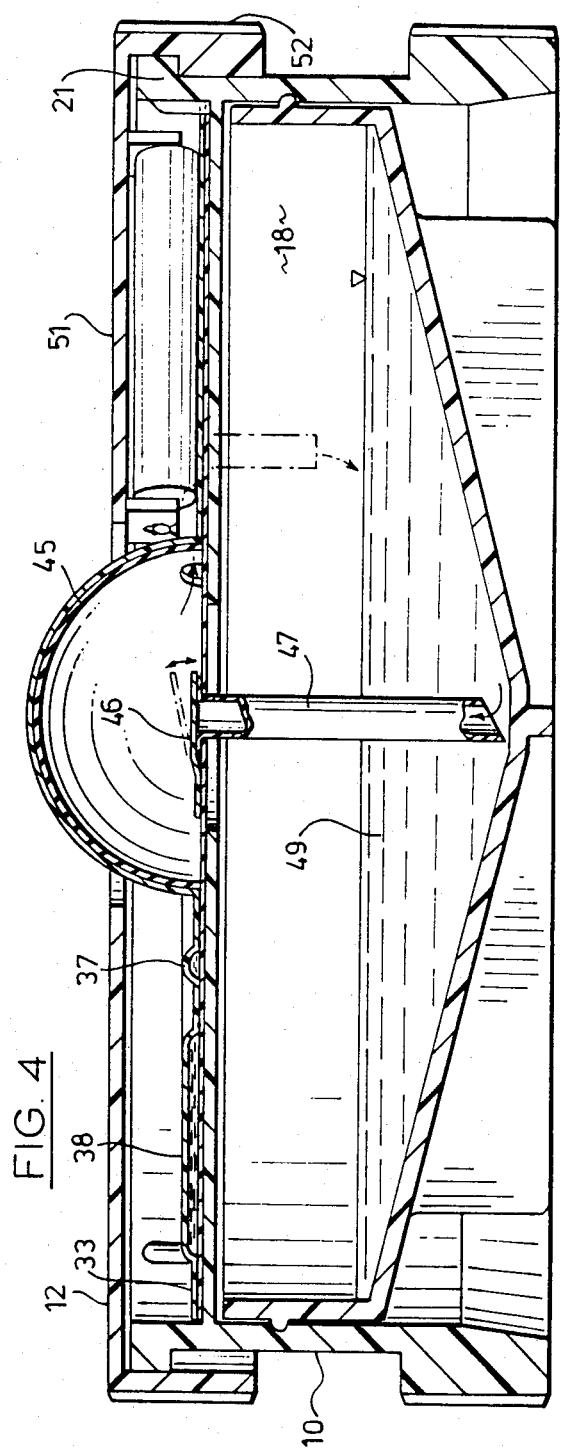
FIG. 4 is a section taken along line 4—4 in FIG. 1 showing the operation of the reservoir, frangible seal and conduit when the forcing means from the cover is applied thereto.

The base 10 has a circular platform 15 which is recessed from the upper rim 16 thereof. A waste reservoir 18 is provided beneath the platform 15 and may be incorporated integrally with the base 10 or may be a separate component. An aperture 19 centrally through the platform 15 provides communication to the waste reservoir 18. The exterior of the base 10 is provided with a flange 21 extending outwardly of the upper rim 16 thereof.

Figures 7, 8:
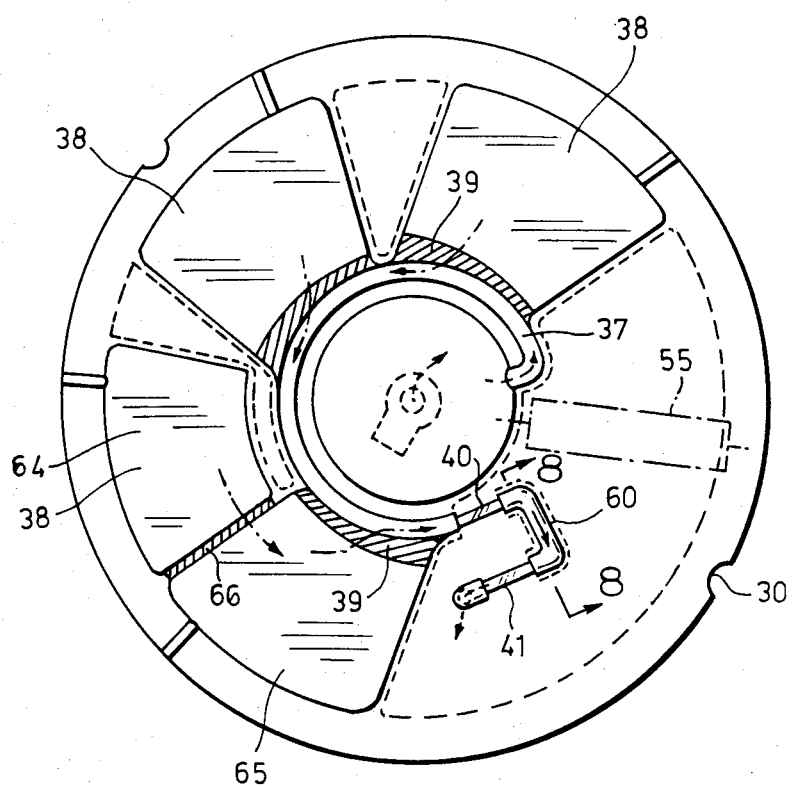
FIG. 7 is a plan view of the disk of the invention.
FIG. 8 is a cross-sectional view at line 8—8 of FIG. 7 showing the emplacement of the assay and reference tubes.

The disk 11 is provided with notches 30 at the circumference thereof which interengage projections 31 formed in the inner wall of the base 10 to position the disk 11 in place on the platform 15. The disk 11 has a flexible membrane 33 attached to the top side thereof. The membrane 33 defines a conduit 37 and a plurality of reagent reservoirs 38 which are separated from the conduit 37 or from one another by frangible seals 39. An assay tube 40 is connected to the exit end of the conduit 37 and may be joined in series to a reference tube 41. Communication is provided to the waste reservoir 18 by means of a conduit 42 which passes through an aperture 43 in the platform 18. As shown in FIGS. 7 and 8, the tubes 40 and 41 may be secured in place by a conduit 60 formed into the surface of the disk 12. Of course, more than one assay tube 40 may be utilized in the device so that a plurality of assays may be conducted simultaneously.

The disk 11 is preferably provided with a test sample recirculation means for causing the sample to contact the inner wall of the assay tube 40 for the desired length of time. As shown in FIGS. 1 and 4, the recirculation means comprises a resiliently flexible dome which in the embodiment illustrated is a hemispherical dome 45 centrally located on the disk 11 and in communication with the entrance end of the conduit 37. A one-way valve 46 is provided at one end of a conduit 47 descending from the central portion of the disk 11. When assembled as shown in FIG. 4, the conduit 47 extends through the central aperture 19 in the base platform 15 and into the waste reservoir 18. Sample liquid 49 introduced into the waste reservoir 18 is pumped through the conduits 47 and 37 and the assay tube 40 by means of the dome 45 and valve 46 which coact as a pump by depressing and releasing the flexible dome 45.

The cover 12 is a short cylindrical structure having a circular top surface 51 and a downwardly extending side wall 52 having an inner diameter just greater than that of the outer diameter of the base 10 at the upper rim 16. The underside of the top surface 51 is preferably provided with a roller 55 extending radially from near the center to near the side wall 52 of the cover 12. The cover has a hole 57 about the center of the top surface 51 of sufficient diameter to accommodate the dome 45.

The cover 12 interacts with the base 10 and disk 11 by means of the roller 55. The roller 55 is of a size and diameter to engage the surface of the disk 11 when the device is assembled as shown in FIG. 4. By rotating the cover 12 when in place on the base 10, the reagent reservoirs 38 are successively emptied through the conduit 37 for the purpose of conducting the assay. The roller 55 may be frustoconical in shape rather than cylindrical to provide a more efficient emptying of the reservoirs 38 as the cover is rotated. The roller 55 extends over the conduit 37.

For the purpose of better understanding the operation of the device of the invention reference will be made to its use as a pregnancy test kit. One type of pregnancy test involves an enzyme immunoassay for the presence of human chorionic gonadotropin (HCG) in the blood or urine. The assay comprises binding the HCG with an enzyme/antibody conjugate wherein the antibody is specific to HCG, i.e. anti-HCG, followed by detection of enzyme activity by determining if enzyme substrate is consumed. If there is no detectable enzyme activity, there was no HCG or sufficient HCG in the test sample for the conjugate to bind to. A preferred enzyme for this assay is urease because the consumption of substrate urea by urease results in the evolution of ammonia causing an increase in pH which may be easily detected by a suitable indicator.

Applying the present device to the HCG assay, the assay tube 40 is first treated to cause a coating of HCG antibody to be bound to the inner wall thereof. The anti-HCG coating is preferably covalently bonded to the wall of the tube 40, but may also be affixed by adsorption. Either method of coating is well known in the art.

The reference tube 41 is not coated with antibody and acts as a colour comparator with the assay tube 40. A sample of urine for testing is introduced into the waste reservoir 18 and the device is assembled for carrying out the assay. The sample is pumped from the reservoir 18 and through the assay tube 40 and reference tube 41 by means of the dome 45 and valve 46 by simply depressing and releasing the dome 45 repeatedly for the required time period.

With the cover 12 in place on the base 10 and with the roller 55 in position before the first reagent reservoir 38, the cover 12 is rotated counterclockwise as shown in FIG. 1 to cause the reagent in the first reservoir 38 to pass into the conduit 37 and through the assay and reference tubes 40 and 41.

Figure 5:
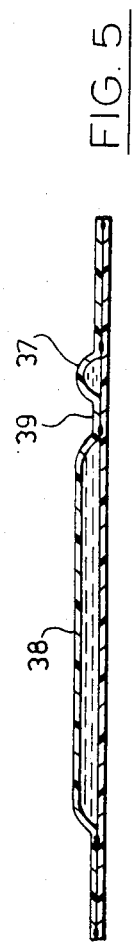
FIGS. 5 and 6 are detail sectional views through a reservoir of the invention showing the operation of the frangible seal.
Figure 6:

As shown in FIGS. 5 and 6, the roller 55 applies pressure to the reservoir 38 causing the frangible seal 39 to break releasing the contents of the reservoir 38 into the conduit 37. Since the conduit 37 is also compressed by the action of the roller 55, the reagent from the reservoir 38 is forced only toward the assay tube 40.

The frangible seals 39 between the reservoir 38 and the conduit 37 are shaped in a generally triangular fashion as shown in FIG. 7 so that the seals 37 rupture continuously rather than all at once as the roller 55 passes over the disk surface. This feature provides a continuous and even flow of reagent through the conduit 37 and the tubes 40 and 41. The roller 55 encounters the narrow end of the triangular frangible seals 39 first, thereby ensuring that rupture occurs at the face of the advancing roller 55 and providing thorough washing of prior reagent from the conduit 37 by the addition of subsequent reagent.

In the present example, the first reagent reservoir 38 is filled with enzyme/antibody conjugate, which in this example is preferably urease/anti-HCG. The anti-HCG portion of the conjugate attaches to the HCG captured in the assay tube 40. The second reservoir 38 contains a wash solution to rid the system of any residual conjugate, and the third reservoir 38 contains a substrate solution for the urease, i.e. urea, and a pH indicator such as bromthymol blue. Of course, each successive reagent is caused to flow through the assay tube 40 by rotation of the cover 12 so as to cause the roller 55 to expel the reservoirs' contents through the frangible seals 39 and conduit 37.

As shown in FIG. 7, the third reagent reservoir 38 preferably comprises two compartments. A first compartment 64 contains reagent liquid for the final step of the assay and a second compartment 65 contains enzyme substrate powder which in this case is urea. Because urea is not stable for long periods in solution, it is preferred to maintain the urea in the stable solid form until it is needed. The compartments 64 and 65 are separated by a thin frangible seal 66 which is ruptured by the pressure on the compartment 64 by the roller 55 thereby allowing the urea powder to be dissolved. The compartment 65 is provided with a frangible seal 39 between it and the conduit 37 which ruptures upon continued rotation of the roller 55 to allow the substrate solution to pass through the tubes 40 and 41.

In the present example, a positive assay results in the development of color in the assay tube 40 after all reservoirs 38 have been emptied. In the case of miniature devices made according to the invention or for quantitative measurements, the color change may be detected by measuring means such as a colorimeter. Otherwise, the color development in the assay tube 40 may be monitored visually through a window (not shown) in the surface 51 of the cover 12.

Additional features of the preferred structure of the device include means associated with the cover 12 for ensuring the proper initial positioning and providing continuous engagement of the roller 55 with the surface of the disk 11. Thus, the inner surface of the side wall 52 of the cover 12 is provided with two projections 71 which fit through correspondingly oriented notches 73 in the flange 21 of the rim 16. The projections 71 and notches 73 are located to ensure the proper initial positioning of the roller 55 before the first reagent reservoir 38. When the cover 12 is rotated, the projections 71 engage the underside of the flange 21 locking the cover 12 on the base 10 (see FIG. 4). To ensure that the cover 12 does not become disengaged until the cover 12 is rotated the full 360° about the rim 16, the projections 71 and notches 73 are not diametrically opposite one another (see FIG. 1).

To reduce the chance of erroneous use of the device, the cover 12 and base 10 may be provided with indicators and click-stops associated with each step in the assay. Thus, after insertion of the sample, the cover 12 would be rotated to the first indicator and click-stop, and then to each successive indicator stop in turn thereby fully completing each step before going on to the next.

As shown in FIG. 3, the roller 55 may be replaced by other means which accomplish the same task such as a solid wiper blade 75. The wiper blade 75 preferably possesses a sufficient degree of resiliency to provide an even and continuous pressure at the surface of the disk 11, and has a rounded or blunt edge 76 for contacting the disk surface.

As shown in FIG. 2, the roller 55 is preferably held in place by the snap fitting of a cylindrical end nib 79 into a bracket 80. The prongs 81 of the bracket 80 define a gap 82 above the snap fit location of the nib 79 which allows the prongs 81 to provide a resilient engagement of the roller 55 in the bracket 80.

It will be apparent to those skilled in this art that the device as described above may be modified in a number of ways. The invention includes all such modifications, and the scope of the present invention is defined in the following claims.

I claim:

1. A device for performing chemical and immunochemical assays, comprising:
    a disk having a thin flexible membrane applied to one side thereof, the membrane coacting with the disk to form a circumferentially disposed conduit having entrance and exit ends and also a plurality of circumferentially disposed reagent reservoirs, the reservoirs being isolated from one another or from the conduit by frangible seals, the frangible seals being arranged to define the desired flow of reagents through the conduit;
    at least one assay tube having entrance and exit ends, the entrance end being attached to the exit end of the conduit, the assay tube having an assay reagent bonded to the inner wall thereof;
    test sample injection means for flowing test sample through the assay tube; and
    means for forcing the contents of each reservoir through the conduit and the assay tube in the desired order by causing the rupture of each frangible seal sequentially, said means preventing back flow of reagent in the conduit.

2. A device as claimed in claim 1, further comprising a waste reservoir in communication with the exit end of the assay tube.

3. A device as claimed in claim 1, further comprising a reference tube connected in series to the assay tube and through which the test sample and all reagents may flow, said reference tube not having an assay reagent bonded to the inner wall thereof.

4. A device as claimed in claim 1, wherein the means for forcing the contents of each reservoir through the conduit and assay tube is a roller.

5. A device as claimed in claim 1, wherein the means for forcing the contents of each reservoir through the conduit and assay tube is a wiper blade.

6. A device as claimed in claim 1, wherein the sample injection means comprises a resiliently flexible dome and a tube with a one way valve, the dome being connectable to the entrance end of the conduit and the tube being capable of having one end immersed in a volume of test sample liquid, the injection means operating to pump the sample through the conduit by repeatedly collapsing and expanding the dome thereby causing suction of the sample liquid through the valve and expulsion of sample into the conduit.

7. A device as claimed in claim 2, wherein the sample injection means comprises a resiliently flexible dome positioned centrally on the disk and in communication with the entrance end of the conduit, a tube extending through the disk beneath the dome and into the waste reservoir so that an end thereof may be immersed in a volume of test sample liquid contained therein, and a one way valve positioned on the disk at the other end of the tube, the dome and valve being capable of coacting to pump sample from the reservoir and through the conduit.

8. A device as claimed in claim 1, wherein one or more reagent reservoirs comprises a liquid containing compartment and a solids containing compartment, the compartments being separated by means of a frangible seal, and the compartments being arranged on the disk so that the means for forcing the reagent reservoirs' contents into the conduit acts first on the liquid containing compartment.

9. A device as claimed in claim 2, wherein the conduit is positioned circumferentially near the center of the disk and the assay tube is positioned longitudinally on the surface of the disk.

10. A device as claimed in claim 9, wherein the exit end of the assay tube is connected to the waste reservoir, and the sample injection means is located about the center of the disk.

11. A device as claimed in claim 1, further comprising a base having a platform for receiving the disk and a cover for the base being rotatable about the base, the cover having said means for forcing the contents of each reservoir through the conduit.

12. A device as claimed in claim 11, further comprising a waste reservoir located beneath the platform, the platform defining an aperture therethrough in communication with the waste reservoir.

13. A device as claimed in claim 12, wherein conduit means are provided from the exit end of the assay tube and through the disk and aperture in the platform.

14. A device as claimed in claim 13, wherein the platform defines an aperture therethrough at the center thereof in communication with the waste reservoir, and the sample injection means comprises a resiliently flexible dome positioned centrally on the disk and in communication with the entrance end of the conduit, a tube extending through the disk beneath the dome through the central aperture in the platform and into the waste reservoir so that an end thereof may be immersed in a volume of test sample liquid contained therein, and a one way valve positioned on the disk at the other end of the tube, the dome and valve being capable of coacting to pump sample from the reservoir and through the conduit.

15. A device as claimed in claim 14, wherein the cover has a roller attached underneath the top surface positioned to engage the disk surface when the device is assembled and to force the contents of each reagent reservoir through the conduit and assay tube upon rotation of the cover about the base.

16. A device as claimed in claim 15, wherein the cover and base have coacting means for positioning the cover and roller at the desired starting point on the disk and said means also locking the cover on the base while allowing unidirectional rotation thereof about the base.

17. A device as claimed in claim 16, wherein the base has a flanged upper rim which is provided with at least two notches for receiving projections located on the inner side surface of the cover, the notches and projections being located to ensure the proper initial orientation of the roller before the first reagent reservoir, and said projections engaging the underside of the flange upon rotation of the cover.

18. A device as claimed in claim 1, wherein the assay reagent is an antibody, antigen or hapten.

* * * * *